United States Patent [19]

Fischer, Jr. et al.

[11] 4,265,239
[45] May 5, 1981

[54] GAS SCAVENGING EXHAUST SYSTEM

[76] Inventors: Charles M. Fischer, Jr., 9260 Alcosta Blvd., Suite D-30, San Ramon, Calif. 94583; Robert S. Price, 3798 Mosswood Dr., Lafayette, Calif. 94549

[21] Appl. No.: 964,086

[22] Filed: Nov. 27, 1978

[51] Int. Cl.³ ............................................. A61M 16/00
[52] U.S. Cl. ................................ 128/205.17; 128/910; 128/207.13
[58] Field of Search ................. 128/188, 145.8, 145.7, 128/145.6, 145.5, 139, 205, 910

[56] References Cited

U.S. PATENT DOCUMENTS

| | | | |
|---|---|---|---|
| 3,348,538 | 10/1967 | Benzel | 128/142 |
| 3,721,239 | 3/1973 | Myers | 128/188 |
| 4,004,585 | 1/1977 | Boehringer | 128/188 |
| 4,015,598 | 4/1977 | Brown | 128/188 |
| 4,151,843 | 5/1979 | Brekke et al. | 128/145.8 X |
| 4,180,066 | 12/1979 | Milliken et al. | 128/205.24 |

OTHER PUBLICATIONS

Foregger, Scaveng-OR Gas Evacuator Illustrations, Air Products, Catalog No. 7-351-005, 6/75, Form No. 4P.

Primary Examiner—Henry J. Recla
Attorney, Agent, or Firm—Allan J. Jacobson; John F. Schipper

[57] ABSTRACT

A system utilizing the central vacuum system in the dental operatory to exhaust analgesic or anesthetic gas from a gas administration assembly. The system includes a nosepiece fitting over the nose of a patient, an exhaust assembly for removing exhaled gas from the nosepiece, and an exhaust chamber formed around the periphery of the nosepiece for scavenging gas leaking through the facial seal at the rim of the nosepiece.

9 Claims, 6 Drawing Figures

U.S. Patent  May 5, 1981  Sheet 1 of 3  4,265,239
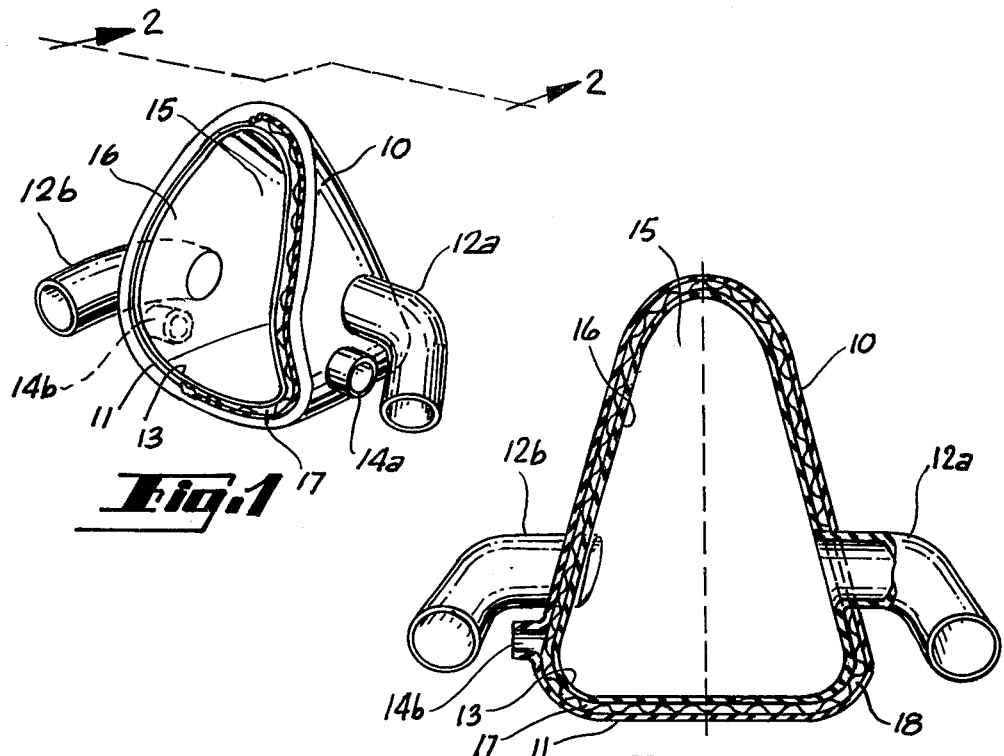
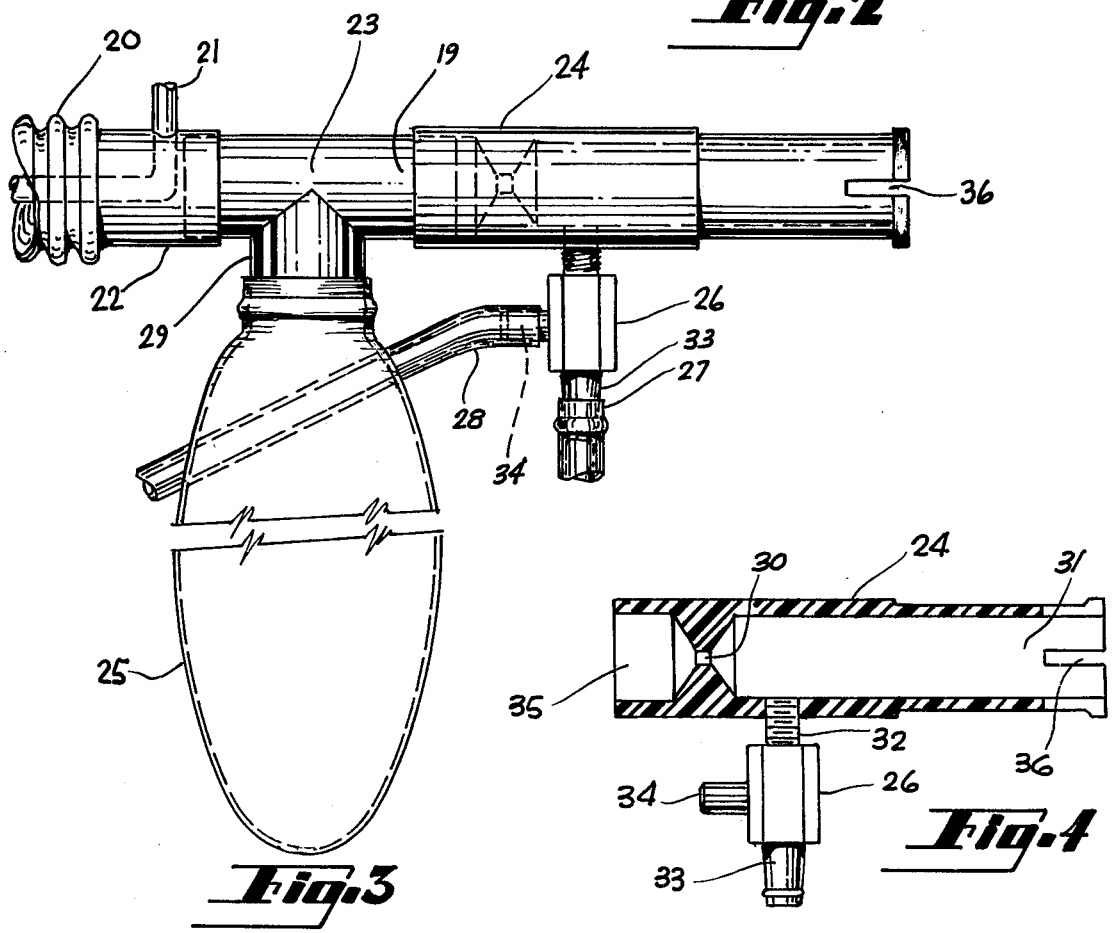

GAS SCAVENGING EXHAUST SYSTEM

FIELD OF THE INVENTION

This invention relates to an exhaust apparatus for gas administration systems, wherein vacuum means are used to remove exhaled and leakage gas.

BACKGROUND OF THE INVENTION

Use of a gaseous analgesic, such as nitrous oxide, in dental work of a potentially painful nature has become widely accepted. Nitrous oxide reduces the patient's sensitivity to pain without rendering the patient unconscious. It can be administered nasally, leaving the mouth unobstructed and free for dental work.

Commonly, nitrous oxide is administered using a nasal inhaler or nosepiece, placed over the patient's nose and connected through appropriate valves to a source of nitrous oxide and oxygen. When the patient inhales, only a small amount of nitrous oxide is absorbed by the lungs; when the patient exhales, most of the nitrous oxide is expelled. The small amount of gas absorbed during analgesia is released shortly after the flow of nitrous oxide terminates. Therefore, substantially all the gas delivered to the patient is ultimately exhaled by the patient. In many previous systems, this gas was simply released into the dental operatory.

Release of nitrous oxide to the environment is undesireable for two reasons. First, there is a tendency for the dentist and other dental office personnel to become anesthetized. Second, exposure to nitrous oxide is an occupational hazard; i.e., studies have shown a probable correlation between routine long-term exposure to nitrous oxide and certain serious diseases. Researchers suspect that the increased rate of spontaneous abortion among female anesthetists, increased incidence of birth defects among children born to anesthetists, and higher rates of disease of the liver and kidney, are related to chronic exposure to waste nitrous oxide. Clearly, a system for administering nitrous oxide without loss of gas to the environment is desirable.

In hospitals, the need to remove or prevent the release of anesthesia in the medical operating room has long been recognized. An anesthetic exhaust system intended to fit existing hospital equipment is described in U.S. Pat. No. 3,721,239 to Myers, wherein a manifold is placed around a conventional pop off valve to vent escaping anesthetic gas to a remote central vacuum.

Recently, a gas scavenging system for the dental operatory has been introduced, as described in U.S. Pat. No. 4,015,595 to Brown. The Brown system includes a first nosepiece disposed within a second nosepiece and a one way pressure relief valve for conducting gas from the inner to the outer nosepiece. Nitrous oxide is supplied to the inner nosepiece, while a vacuum source is connected to the region between the first and second nosepieces. In the Brown circuit, the analgesic effect varies inversely with the scavenging effect: as the vacuum flow is increased, the level of analgesic effect is reduced. The system is particularly sensitive to fluctuations in vacuum and is therefore difficult to adjust to a proper balance between analgesic effect and scavenging effect.

Another type of gas administration system is the Allen circuit, made by Dupaco, San Marcos, Calif. The Allen circuit has a pressure operated, one way exhalation valve that senses the increased pressure when the patient exhales. When the nosepiece pressure rises above a predetermined level the exhaust valve opens to remove gas. Pressurized gas inside the nosepiece tends to lift the nosepiece away from the face, causing gas leaks. The Allen circuit uses no edge scavenging means and relies on a snug fit between the mask and the patient's face to prevent the loss of gas.

In the above described system, there is no provision for air intake in the event that the gas supply system fails or where the patient requires a high inspiratory demand. Thus, a higher gas flow is necessary, resulting in greater use of nitrous oxide.

SUMMARY OF THE INVENTION

The present invention is a gas exhaust system used in an assembly for administering gas to a patient. The exhaust system uses vacuum means to scavenge gas leaking through the edge of a nosepiece as well as to remove exhaled gas from the system generally.

Adjacent to the rim of the nosepiece is a peripheral exhaust chamber connected to a source of vacuum. Any leakage gas is swept into the peripheral exhaust chamber and thereby scavenged. The peripheral exhaust chamber is connected to an exhaust assembly that regulates the vacuum supplied thereto. The exhaust assembly also functions to remove scavenged and exhaled gas from the system.

The exhaust assembly comprises a resistance means for creating a resistance to gas flow and a divider means for dividing gas flow. The resistance means is placed at the exhaust port, where gas is to be exhausted from the system, to prevent the flow of exhaled gas from exceeding the vacuum flow capability. Connecting the system together, the divider means communicates with (1) the resistance means, (2) the peripheral exhaust chamber of the nosepiece, (3) the ambient atmosphere and (4) a source of vacuum. Flow induced by the vacuum is dynamically adjusted and divided between flows from the peripheral exhaust chamber, the ambient atmosphere and the exhaust port. The resistance means can be bidirectional so that air can be drawn into the system on demand if necessary.

Accordingly, an object of the present invention is to provide an efficient and versatile gas exhaust system that may be used in a variety of gas circuits, including both rebreathing and non-rebreathing circuits.

A further object of the invention is to provide a means for scavenging gas leakage through the facial seal at the rim of a nosepiece wherein the scavenging effect, as well as the analgesic effect, is relatively independent of fluctuations in vacuum pull.

A further object of the invention is to provide a gas exhaust system that requires no valve and provides for air intake into the system on demand.

Other objects of the invention and advantages thereof will become clear from reference to the detail description and the accompanying drawings.

BRIEF DESCRIPTION OF THE DRAWINGS

FIG. 1 is an isomeric view of the assembled nosepiece and jacket.

FIG. 2 is a dual level cross-sectional view of the assembled nosepiece and jacket.

FIG. 3 shows the exhaust assembly embodying the present invention connected to a gas reservoir in a gas breathing circuit.

FIG. 4 is a cross-sectional view of the exhaust assembly shown in FIG. 3.

DETAILED DESCRIPTION

Figure 5:
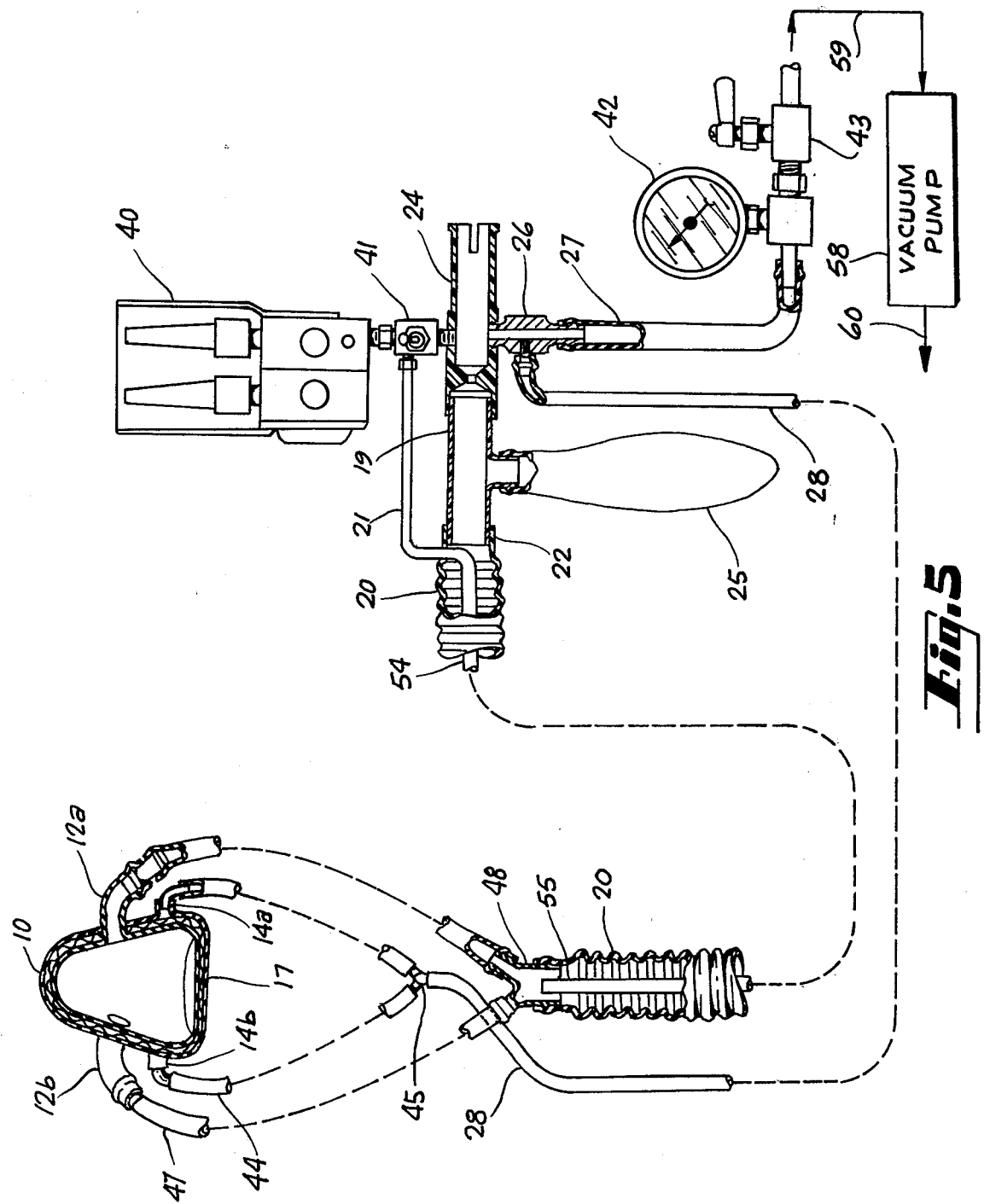
FIG. 5 shows an embodiment of the present invention used in a rebreathing gas circuit.

As assembled face mask is shown in FIG. 1. A cross-sectional view is shown in FIG. 2. The assembly comprises a nosepiece 16, a jacket 10, gas conduit means 12a, 12b, and vacuum conduit means 14a, 14b. The nosepiece 16 is a cup-shaped structure of soft flexible material. The jacket 10 fits snugly over the nosepiece 16, to form a peripheral exhaust chamber 17. Gas is supplied to the interior of the nosepiece 16 through conduits 12a and 12b, and a source of vacuum is supplied to the peripheral exhaust chamber through conduits 14a and 14b.

The mask is placed over the nose of the patient and secured by a strap or similar means (not shown). The rim 13 of the nosepiece 16 follows the contour of the patient's face and forms a seal with the patient's face. Thus, the space between the nosepiece and the nose forms a central gas chamber 15 for receiving gas from and delivering gas to the patient. The rim of the jacket 10 is shaped similarly to the rim 13 of the nosepiece to effect a seal at the patient's face.

In use, the analgesic mixture of nitrous oxygen and oxygen is supplied through the conduit means 12a, 12b to the gas chamber 15. The peripheral exhaust chamber communicates with the source of vacuum through conduit means 14a, 14b. Any leakage gas, defined as gas leaking through the seal at the rim 13 of the nosepiece 16, is swept into the peripheral exhaust chamber 17 and toward the source of vacuum. Bumps 18 on the interior of the jacket 10 act as a spacer means to help keep the peripheral exhaust chamber from collapsing under the influence of the vacuum. Since the vacuum circuit that is connected to the peripheral exhaust chamber (as discussed hereinafter), is separate from the gas circuit connected to the nosepiece, the analgesic effect is independent of the scavenging effect.

FIG. 3 shows the exhaust assembly connected to a gas breathing circuit. Here, the breathing circuit is of the re-breathing type and contains a reservoir bag 25. The reservoir bag 25 holds a mixture of fresh gas and previously exhaled gas. The exhaust assembly, which includes an exhaust tube 24 and a tee divider 26, is connected to the breathing circuit and to the reservoir 25 by a tee connection 23. Generally, a tee divider is any three-part flow divider means. One end 19 of the tee 23 is the exhaust port of the system, i.e., the end point of the system at which gas is to be removed. Another end of the tee 23 is connected to the corrugated hose 20 and the third tee end, stem 29, connects with the reservoir 25.

A cross-sectional view of the exhaust assembly is shown in FIG. 4. The assembly comprises a resistance means and a divider means. Here, the resistance means is simply a restricted opening 30 in a channel through an exhaust tube 24. The exhaust tube 24 communicates with the exhaust port 19 (FIG. 3) at end 35 near the resistance means 30, and the other end 31 of the channel is open to the atmosphere. Communicating with the exhaust tube 24 through the wall thereof is the tee divider 26. It can be seen that the divider means is the tee divider 26 in combination with the open half 31 of the exhaust tube 24. The stem 34 of the tee 26 is connected by a hose 28 (FIG. 5) to the conduit 14a, 14b to provide a vacuum pull for the peripheral exhaust chamber of the mask. A vacuum supply, which can be the central vacuum system commonly found in dental offices, is connected to the system at one end 33 of the tee 26 by a hose 27. Basically, the divider means serves to divide the vacuum-induced flow into three components: (1) exhaled gas from the exhaust port 19; (2) leakage gas from the peripheral exhaust chamber 17 of the face mask; and (3) air from the ambient atmosphere. These three components are dynamically adjusted by the gas exhaust assembly to satisfy breathing system demands, as will become clear from the following description of system operation.

Hose fittings such as to the tee divider 26, or fittings between the exhaust tube 24 and the tee connection 23, are friction fittings that rely on a snug fit for a gas tight seal. The fitting on the tee divider 26 at the end 32 that communicates with the exhaust tube 24 can also be a friction fitting as well as a threaded fitting.

To review the operation of the exhaust system, first assume that the reservoir 25 is empty, the vacuum supply connected, and the gas breathing circuit turned on. Initially, the vacuum flow will draw a gas flow through the open end 31 of the exhaust tube 24.

If the patient inhales when the reservoir 25 is empty, air will be drawn through the open end 31 of the exhaust tube 24 into the system. The end 31 is provided with cutouts 36 to prevent accidental blockage of air. When the patient begins to exhale, the restricted opening 30 will create a slight back pressure, causing reservoir bag 25 to begin to fill up. The reservoir 25, which is a high compliance bag, will then expand to about two liters at a pressure of less than 0.5 centimeters of water. As the bag 25 fills with exhaled gas, the flow of gas is divided: part of the exhaled gas goes through the restricted opening 30, and part goes into the bag 25. The gas entering the exhaust tube 24 through the restricted opening 30 is swept away through the tee divider 26 toward the source of the vacuum. After the reservoir bag 25 fills beyond some point, most additional exhaled gas will pass through the restricted opening 30 and be exhausted away from the system.

When the patient next inhales, some of the contents of the reservoir will be used to supply gas to the patient. At all times, as long as the reservoir 25 is partly filled, some gas will spill into the exhaust tube 24.

There is some contribution to exhaust flow from the peripheral exhaust chamber 17 (FIG. 2) of the face mask. Any gas entering the chamber 17 will be swept away via hose 28 (FIG. 3). The major flow is from the open end 31 of the exhaust tube 24; but minor gas flow, from the peripheral chamber of the face mask to the stem 34 of the tee divider 26, is also present. Increases in exhaled gas flow through the restricted opening 30 will result in less air flow into the open end 31 of the exhaust tube 24. If, as described before, air is required by the patient, more air will flow into the exhaust tube 24. For proper balance, the restricted opening 30 must provide a resistance large enough to restrict exhaled gas flow to the flow capability of the vacuum supply. The resistance must also be large enough to allow partial filling of the reservoir bag 25. On the other hand, the resistance must be small enough to allow comfortable air intake by the patient as required.

Gas flow is always maintained through the open end 31 of the exhaust tube 24 so that no part of the system is exposed to the full negative pressure of the vacuum. For example, even if the face mask momentarily seats perfectly against the patient's face, the negative pressure in the peripheral exhaust chamber will be limited to a safe value between minus 8 and minus 10 centimeters of water. Also, the restricted opening 30 protects the breathing circuit from exposure to a negative pressure.

From the foregoing, it will be seen that the exhaust assembly dynamically divides and adjusts gas flow to meet all system conditions.

FIG. 5 shows the exhaust system used in a gas rebreathing circuit. A conventional gas source 40 supplies nitrous oxide and oxygen to an on/off switch 41. The output end of the switch 41 is connected via a tube 21 through the wall 22 to a flexible gas delivery tube 54. The gas delivery tube 54 is disposed lengthwise within a larger flexible corrugated hose 20. At the far end 55 of the gas tube 54 where fresh gas is dumped into the breathing circuit, is a "Y" connection 48 where the gas conduit means 12a, 12b communicates with the gas tube and the flexible, corrugated hose 20. When the patient inhales, fresh gas is supplied by the gas delivery tube 54. Exhaled gas travels up the hose 20 to fill the reservoir 25. During the pause following expiration, fresh gas enters the hose 20 at the end 55 of the gas tube 54. This helps push the exhaled carbon dioxide gas toward the exhaust assembly. Gas stored in the reservoir is rebreathed during the next inspiratory phase. The concentric hose and tube arrangement described above is known as the bain tube, the operation of which is well known to those skilled in the art.

Connecting the peripheral exhaust chamber 17 of the mask to the tee fitting 26 on the exhaust assembly are two hoses 44, a "Y" connection 45, and a hose 28. The exhaust tube 24 and the tee divider 26 cooperate with the exhaust port 19 of the system and the peripheral exhaust chamber 17 of the mask in the manner previously described. Observe that the system of FIG. 5 has no valves but still provides for rebreathing stored gas and for air intake in the event that the gas source fails.

The vacuum-induced flow removes exhaled and scavenged gas from one end of the tee 26, through hose 27, through a flow rate indicator 42, through a flow rate adjustment valve 43, thence to a hose 59. The vacuum pump 58, exhausts gas through a hose 60 to a point remote from the dental operatory.

Figure 6:
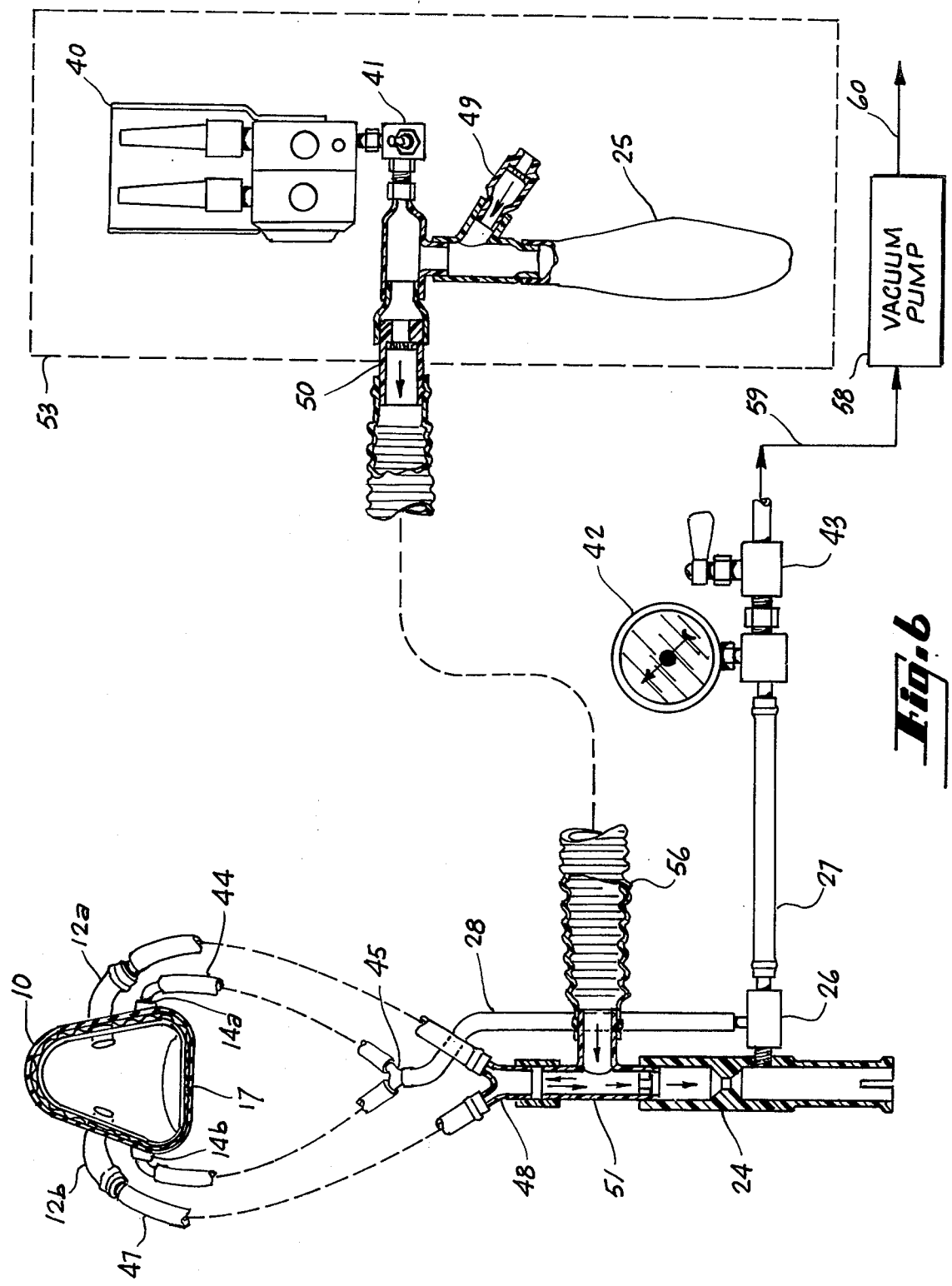
FIG. 6 shows an embodiment of the present invention used in a non-rebreathing gas circuit.

Another gas breathing circuit employing the invented exhaust system is shown in FIG. 6, where gas is breathed only once and is exhausted from the system. A conventional gas source 40, on/off switch 41, and reservoir are used, and two unidirectional valves 49 and 50 are employed to form a conventional gas supply 53. Valve 49 provides for air intake into the system, if required by the patient. Valve 50 is included to guarantee that exhaled gas does not flow back into the gas supply assembly. In this circuit the reservoir bag 25 functions only to store fresh gas from the source 40, thus easing the peak flow required for the application.

A flexible, corrugated hose 56 delivers gas to the conduit means 12a, 12b through hose 47 and "Y" connector 48. A third unidirectional valve 51, communicating with the gas hose 56, acts as the exhaust port of the system.

When the patient inhales, valve 50 opens to conduct gas to the patient, and valve 51 closes. When the patient exhales, the resulting pressure closes valve 50 and opens valve 51, allowing exhaled gas to enter the exhaust assembly. The exhaust assembly functions exactly as in the previous system of FIG. 5, except that the unidirectional valve 51 allows no air to be taken into the system through the exhaust assembly.

Although the best mode for making and using the invention has been shown and described herein, it should be clear that modification and variation can be made without departing from what is considered to be the subject matter of the invention. For example, the resistance means could be a wire mesh, and the divider means might be a one-piece four-way divider. Accordingly, the present embodiments are to be considered as illustrative and not restrictive of the scope of the invention.

What is claimed is:

1. In a gas supply system for administering gas to a patient, the system having a remote vacuum means, a scavenging mask with a peripheral chamber adjacent to the rim of the mask, means for supplying gas to the mask, means for removing exhaled gas from the mask, and an exhaust port communicating with the mask through the means for removing exhaled gas, an improved exhaust assembly comprising:

A. resistance means communicating with the exhaust port for creating a resistance to gas flow therefrom, said resistance means comprising an exhaust tube having a first end, a second end, and a channel therethrough, said channel having a restricted opening near the first end thereof so as to provide resistance to gas flow; and B. divider means for dividing gas flow, the divider means communicating with the resistance means, with the peripheral chamber, with the ambient atmosphere, and with the remote vacuum means so that the vacuum-induced gas flow is divided between exhaled gas from the exhaust port, scavenged gas from the peripheral chamber and air from the ambient atmosphere, wherein said divider means includes the second end of said exhaust tube wherein said second end is open to the ambient atmosphere and a tee divider having two ends and a stem, the tee divider communicating at one end with the exhaust tube through the tube wall between the restricted opening and said second end of the exhaust tube communicating with the ambient atmosphere, the tee divider communicating at the other end with said remote vacuum means, the tee divider communicating at the stem thereof with said peripheral chamber.

2. A rebreathing gas supply system for administering gas to a patient, the system comprising:

A. a mask comprising:
   a. a nosepiece arranged to fit over the patient's nose to form a central chamber adjacent to the patient's face, the nosepiece being shaped so that the rim thereof effects a seal between the nosepiece and the patient's face;
   b. first conduit means connected to the nosepiece for conducting gas to and from the central chamber;
   c. a jacket fitting snugly over the nosepiece, the jacket being formed with openings for the first conduit means to pass therethrough, the jacket rim being spaced adjacent to the rim of the nosepiece so as to form a peripheral chamber for receiving gas leaking through the seal between the nosepiece and the patient's face; and
   d. second conduit means connected to the jacket and communicating with the peripheral chamber for conducting leakage gas therefrom;

B. a breathing circuit connected to the other end of the first conduit means, the circuit including means for supplying gas thereto, means for removing exhaled gas therefrom, and means for storing at least a portion of the exhaled gas, the storing means including means for reintroducing stored gas into said other end of the first conduit means for rebreathing by the patient; and C. an exhaust assembly comprising:
 a. an exhaust tube having a first end, a second end and a channel therethrough, the channel being narrower near the first end so as to form a restricted opening for resistance to gas flow, the exhaust tube being connected at the first end to the means for storing gas and to said other end of said first conduit means, said exhaust tube being open at the second end to the ambient atmosphere;
 b. a tee divider having two ends and a stem, the tee divider communicating at one end thereof with the exhaust tube through the tube wall between the restricted opening and said second end of the exhaust tube communicating with the ambient atmosphere;
 c. means for connecting the stem of the tee divider to the second conduit means so that the stem is in flow communication with the peripheral chamber of the mask; and
 d. means connected to the second end of the tee divider for supplying a source of vacuum thereto so that the vacuum source causes a gas flow that is dynamically composed of scavenged gas received from the peripheral chamber, of exhaust gas being removed from the storing means and of ambient air being drawn from the open end of the exhaust tube.

3. Apparatus according to claim 2, wherein said means for storing rebreathed gas includes a gas reservoir bag.

4. Apparatus according to claim 3, wherein said means for exhausting gas includes a flexible hose communicating at one hose end with said first conduit means and communicating at the second hose end with said reservoir bag.

5. Apparatus according to claim 4, wherein said means for supplying gas includes a source of gas and a flexible tube disposed lengthwise inside said flexible hose, the flexible tube communicating at one end thereof through the wall of said flexible hose to the source of gas and communicating at the second end with said first conduit means, for conducting gas to the nosepiece.

6. In a rebreathing gas supply system for administering gas to a patient, the system having a remote vacuum system and a breathing circuit, the breathing circuit including means for supplying gas, means for removing exhaled gas, and means for storing at least a portion of the exhaled gas, the storing means including means for re-introducing the stored gas into the breathing circuit for rebreathing by the patient, an improvement comprising:

A. a mask comprising:
 a. a nosepiece arranged to fit over the patient's nose to form a central chamber adjacent to the patient's face, the nosepiece being shaped so that the rim thereof effects a seal between the nosepiece and the patient's face;
 b. first conduit means connected at one end thereof to the nosepiece, for conducting gas to and from said central chamber, the first conduit means communicating with the breathing circuit;
 c. a jacket fitting snugly over the nosepiece, the jacket being formed with openings for the first conduit means to pass therethrough, the jacket rim being spaced adjacent to the rim of the nosepiece so as to form a peripheral chamber for receiving gas leaking through the seal between the nosepiece and the patient's face; and
 d. second conduit means connected to the jacket and communicating with the peripheral chamber, for conducting leakage gas therefrom; and B. an exhaust assembly comprising:
 a. an exhaust tube having a first end, a second end and a channel therethrough, the channel being narrower near the first end so as to form a restricted opening for resistance to gas flow, the exhaust tube being connected at the first end to the means for storing gas and to the other end of said first conduit means, said exhaust tube being open at the second end to the ambient atmosphere;
 b. a tee divider having two ends and a stem, the tee divider communicating at one end thereof with the exhaust tube through the tube wall between the restricted opening and said second end of the exhaust tube communicating with the ambient atmosphere;
 c. means for connecting the stem of the tee divider to the second conduit means so that the stem is in flow communication with the peripheral chamber of the mask; and
 d. means connected to the other end of the tee divider, for supplying a source of vacuum thereto so that the vacuum draws a gas flow dynamically composed of scavenged gas received from the peripheral chamber, of exhaled gas being removed from the storing means and of ambient air being drawn through the open end of the exhaust tube.

7. A non-rebreathing gas supply system for administering to a patient, the system comprising:

A. a mask comprising:
 a. a nosepiece arranged to fit over the patient's nose forming a central chamber adjacent to the patient's face, the nosepiece the nosepiece being shaped so that the rim thereof effects a seal between the nosepiece and the patient's face;
 b. first conduit means connected at one end thereof to the nosepiece for conducting gas to and from the central chamber;
 c. a jacket fitting snugly over the nosepiece, the jacket being formed with openings for the first conduit means to pass therethrough, the jacket rim being spaced adjacent to the rim of the nosepiece so as to form a peripheral chamber for receiving gas that leaks through the seal between the nosepiece and the patient's face; and
 d. second conduit means connected to the jacket and communicating with the peripheral chamber for conducting leakage gas therefrom;

B. means for supplying gas to the other end of the first conduit means, the gas supply means being responsive to the patient by conducting gas through the first conduit means whenever the patient inhales;

C. means for exhausting gas from the first conduit means, the exhausting means being responsive to the patient by exhausting gas from the first conduit means whenever the patient exhales; and D. an exhaust assembly comprising:
  a. an exhaust tube having a first end, a second end and a channel therethrough, the channel being narrower near the first end so as to form a restricted opening for resistance to gas flow, the exhaust being connected at the first end to the means for exhausting gas and to said other end of said first conduit means, said exhaust tube being open at the second end to the ambient atmosphere;
  b. a tee divider having two ends and a stem, the tee divider communicating at one end thereof with the exhaust tube through the tube wall between the restricted opening and said second of the exhaust tube communicating with the ambient atmosphere;
  c. means for connecting the stem of the tee divider to the second conduit means so that the stem is in flow communication with the peripheral chamber of the mask; and
  d. vacuum means connected to the other end of the tee divider for supplying a source of vacuum thereto so that the vacuum source draws a gas flow of scavenged gas received from the peripheral chamber, of exhaled gas being removed from the nosepiece and of ambient air being drawn through the open end of the exhaust tube.

8. Apparatus according to claim 7, wherein said means for exhausting gas includes a unidirectional valve, the valve communicating with said first conduit means so that increasing gas pressure during patient exhalation opens the valve to exhaust gas therethrough.

9. In a non-rebreathing gas supply for administering gas to a patient, the system having means for supplying gas, the supply means being responsive to the patient inhaling, means for exhausting gas, the exhaust means being responsive to the patient exhaling, and a remote vacuum system, an improvement comprising:
  A. a mask comprising:
    a. a nosepiece arranged to fit over the patient's nose to form a central chamber adjacent to the patient's face, the nosepiece being shaped so that the rim thereof effects a seal between the nosepiece and the patient's face; and
    b. first conduit means connected to the nosepiece at one end thereof for conducting gas to and from the central chamber, the first conduit means communicating at the other end thereof with the gas supply means and with the gas exhaust means;
    c. a jacket fitting snugly over the nosepiece, the jacket being formed with openings for the first conduit means to pass therethrough, the jacket rim also being spaced adjacent to the rim of the nosepiece so as to form a peripheral chamber for receiving gas leaking through the seal between the nosepiece and the patient's face; and
    d. second conduit means connected to the jacket and communicating with the peripheral chamber for conducting leakage gas therefrom; and
  B. an exhaust assembly comprising:
    a. an exhaust tube having a first end, a second end and a channel therethrough, the channel being narrower near the first end so as to form a restricted opening for resistance to gas flow, the exhaust tube being connected at the first end to the means for exhausting gas and to the other end of said first conduit means, said exhaust tube being open at the second end to the ambient atmosphere;
    b. a tee divider having two ends and a stem, the tee divider communicating at one end thereof with the exhaust tube through the wall of said exhaust tube between the restricted opening and said second end of the exhaust tube communicating with the ambient atmosphere;
    c. means for connecting the stem of the tee divider to the second conduit means so that the stem is in flow communication with the peripheral chamber of the mask; and
    d. means connected to the other end of the tee divider for connecting the remote vacuum system thereto so that the vacuum source draws a gas flow of scavenged gas received from the peripheral chamber, of exhaled gas being removed from the nosepiece and of ambient air being drawn from the open end on the exhaust tube.

* * * * *